US009155808B2

(12) United States Patent
Moglan et al.

(10) Patent No.: US 9,155,808 B2
(45) Date of Patent: Oct. 13, 2015

(54) RADIATION SOURCE ASSEMBLY

(75) Inventors: Cristian Moglan, London (CA);
Christopher Sheculski, London (CA)

(73) Assignee: Trojan Technologies, London (CA)

( * ) Notice: Subject to any disclaimer, the term of this patent is extended or adjusted under 35 U.S.C. 154(b) by 0 days.

(21) Appl. No.: 13/821,786

(22) PCT Filed: Sep. 12, 2011

(86) PCT No.: PCT/CA2011/001025
§ 371 (c)(1),
(2), (4) Date: May 23, 2013

(87) PCT Pub. No.: WO2012/037644
PCT Pub. Date: Mar. 29, 2012

(65) Prior Publication Data
US 2013/0234037 A1    Sep. 12, 2013

Related U.S. Application Data

(60) Provisional application No. 61/344,680, filed on Sep. 10, 2010.

(51) Int. Cl.
| | | |
|---|---|---|
| *G01N 23/10* | (2006.01) |
| *A61L 2/10* | (2006.01) |
| *C02F 1/32* | (2006.01) |
| *H01R 33/76* | (2006.01) |
| *H01R 13/625* | (2006.01) |

(52) U.S. Cl.
CPC . *A61L 2/10* (2013.01); *C02F 1/325* (2013.01); *H01R 33/76* (2013.01); *C02F 2201/004* (2013.01); *C02F 2201/3225* (2013.01); *C02F 2303/14* (2013.01); *H01R 13/625* (2013.01)

(58) Field of Classification Search
None
See application file for complete search history.

(56) References Cited

U.S. PATENT DOCUMENTS

| | | | | |
|---|---|---|---|---|
| 6,039,460 A  * |  3/2000 | Ng et al. | ........................ | 362/267 |
| 6,090,296 A  * |  7/2000 | Oster | ....................... | 210/748.12 |
| 6,228,332 B1 * |  5/2001 | Dunn et al. | ................ | 422/186.3 |
| 7,741,617 B2 * |  6/2010 | Matthews et al. | ........ | 250/455.11 |
| 2005/0247609 A1 * | 11/2005 | Laing et al. | .................... | 210/109 |
| 2007/0284540 A1 * | 12/2007 | Matthews et al. | ............. | 250/436 |
| 2008/0044320 A1 * |  2/2008 | Traubenberg et al. | ..... | 422/186.3 |

FOREIGN PATENT DOCUMENTS

WO    2007/078294 A1    7/2007

OTHER PUBLICATIONS

International Search Report for International Application No. PCT/CA2011/001025 with a date of mailing of Jan. 5, 2012.

* cited by examiner

*Primary Examiner* — Andrew Smyth
(74) *Attorney, Agent, or Firm* — Katten Muchin Rosenman LLP

(57) ABSTRACT

There is described a radiation source assembly comprising an elongate radiation source; a reactor port for receiving and reversibly securing the elongate radiation source; a top plug element for reversible connection to a proximal end of the radiation source and reversible engagement with the reactor port; the top plug element configured to be disengaged from reactor port without disengagement of the elongate radiation source from the reactor port.

19 Claims, 14 Drawing Sheets

RADIATION SOURCE ASSEMBLY

CROSS-REFERENCE TO RELATED APPLICATION

The present application claims the benefit under 35 U.S.C. §119(e) of provisional patent application Ser. No. 61/344,680, filed Sep. 10, 2009, the contents of which are hereby incorporated by reference.

FIELD OF THE INVENTION

In one of its aspects, the present invention relates to a radiation source assembly. In another of its aspects, the present invention relates to a radiation source module comprising a plurality of radiation source assemblies. Other aspects of the invention will become apparent to those of skill in the art upon reviewing the present specification.

DESCRIPTION OF THE PRIOR ART

Fluid treatment systems are known generally in the art.

For example, U.S. Pat. Nos. 4,482,809, 4,872,980 and 5,006,244 [all in the name of Maarschalkerweerd and hereinafter referred to as the Maarschalkerweerd Patents] all describe gravity fed fluid treatment systems which employ ultraviolet (UV) radiation.

Such systems include an array of UV lamp frames which include several UV lamps each of which are mounted within sleeves which extend between and are supported by a pair of legs which are attached to a cross-piece. The so-supported sleeves (containing the UV lamps) are immersed into a fluid to be treated which is then irradiated as required. The amount of radiation to which the fluid is exposed is determined by the proximity of the fluid to the lamps, the output wattage of the lamps and the fluid's flow rate past the lamps. Typically, one or more UV sensors may be employed to monitor the UV output of the lamps and the fluid level is typically controlled, to some extent, downstream of the treatment device by means of level gates or the like.

In recent years, there has been interest in the so-called "transverse-to-flow" fluid treatment systems. In these systems, the radiation source is disposed in the fluid to be treated in a manner such that the longitudinal axis of the radiation source is in a transverse (e.g., substantially orthogonal or vertical orientation of the radiation sources) relationship with respect to the direction of fluid flow past the radiation source. See, for example, any one of:

International Publication Number WO 2004/000735 [Traubenberg et al.];

International Publication Number WO 2008/055344 [Ma et al.];

International Publication Number WO 2008/019490 [Traubenberg et al.];

U.S. Pat. No. 7,408,174 [From et al.];

U.S. provisional patent application Ser. No. 61/193,686 [Penhale et al.], filed Dec. 16, 2008; and U.S. provisional patent application Ser. No. 61/202,576 [Penhale et al.], filed Mar. 13, 2009.

When it becomes necessary to service the lamp (e.g., to replace it after its service life has been or is about to be exceeded), it is commonly necessary to remove the radiation source assembly from the fluid treatment system and effectively disassemble it to access the various components.

As is known in the art, a significant amount of electrical power is used to operate the lamps in the fluid treatment systems referred to above and it is know those lamps emit large amounts of ultraviolet radiation which is harmful to humans. When it becomes necessary to service the lamp and remove it from the fluid treatment system, it is necessary to disconnect the power supply to the lamp. Historically, the prior art has not been focussed on safe disconnection of power from the lamp during servicing thereof. Thus, for example, it has been common practise to remove the lamp from the fluid treatment system while it is still connected to the power supply and thereafter to disconnect the power supply from the lamp.

While proper operating procedure typically necessitates that all power to the lamp be turned off prior to removal of the lamp from the fluid treatment system, there is always the possibility that, through inadvertence or mistake, the power supply is not turned off and the lamp is removed from the fluid treatment system while it is still "hot"—i.e., emitting harmful ultraviolet radiation. This is quite dangerous and can lead to catastrophic results for the service operator. Particularly, the potential for exposure to ultraviolet radiation creates an occupational health problem for the service operator who fails to turn off the power to the lamp prior to servicing thereof.

Accordingly, it would be desirable to have a radiation source assembly that obviates or mitigates at least one of the above-mentioned problems of the prior art. More particularly, it would be desirable to have a radiation source assembly which was configured to require that power to the radiation source (e.g., lamp) in the assembly be disconnected prior to being able to remove the radiation source from the fluid treatment system. Such a radiation source assembly would have improved safety and reduce potential occupational health risks associated with the prior art approach described above.

SUMMARY OF THE INVENTION

It is an object of the present invention to obviate or mitigate at least one of the above-mentioned disadvantages of the prior art.

It is another object of the present invention to provide a novel radiation source assembly.

It is another object of the present invention to provide a novel radiation source module.

It is another object of the present invention to provide a novel fluid treatment system.

Accordingly, in one of its aspects, the present invention provides a radiation source assembly comprising:

an elongate radiation source;

a reactor port for receiving and reversibly securing the elongate radiation source;

a top plug element for reversible connection to a proximal end of the radiation source and reversible engagement with the reactor port; the top plug element configured to be disengaged from reactor port without disengagement of the elongate radiation source from the reactor port.

The invention also relates to a radiation source module and to a fluid treatment system incorporating this radiation source assembly.

Thus, the present inventors have developed a novel radiation source assembly which obviates or mitigates one or more of the above-mentioned problems of the prior art. Specifically, the present radiation source assembly is configured such that the power supply to the elongate radiation source must be disconnected prior to the service operator being able to remove the elongate radiation source from the fluid treatment system. By configuring the radiation source assembly to require such a two step operation, safety is improved and potential occupational health risks are obviated or mitigated.

In a preferred embodiment of the present radiation source assembly, additional advantageous concerning safety accrue from the provision of a means for the service operator to know if the radiation source assembly is flooded with high pressure fluid prior to disconnection of the power from the elongate radiation source.

Other advantages of the invention will become apparent to those of skill in the art upon reviewing the present specification.

BRIEF DESCRIPTION OF THE DRAWINGS

Embodiments of the present invention will be described with reference to the accompanying drawings, wherein like reference numerals denote like parts, and in which.

DETAILED DESCRIPTION OF THE PREFERRED EMBODIMENTS

Figure 1:
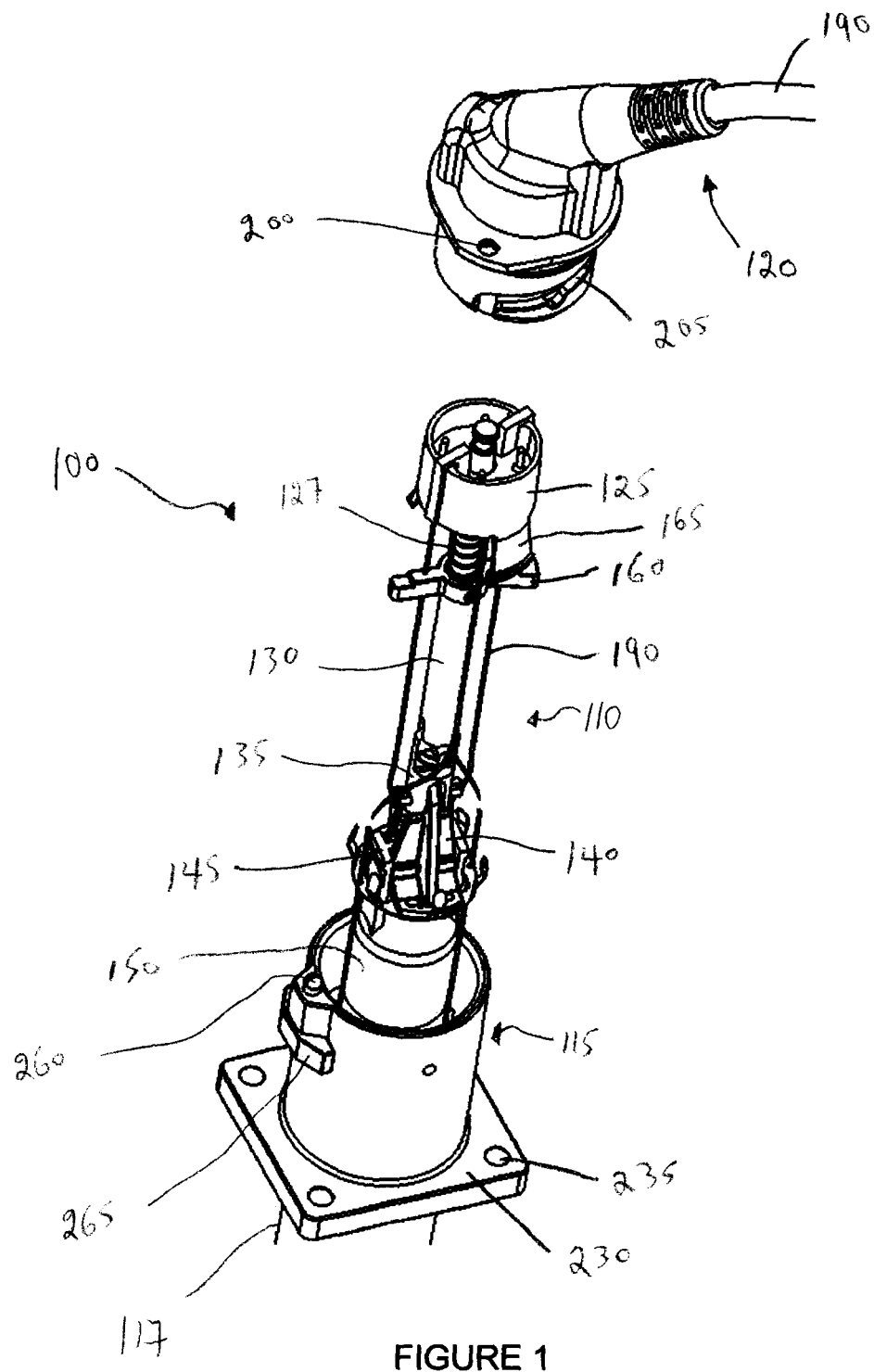
FIG. 1 illustrates a perspective view of a preferred embodiment of the present radiation source assembly.
Figure 2:
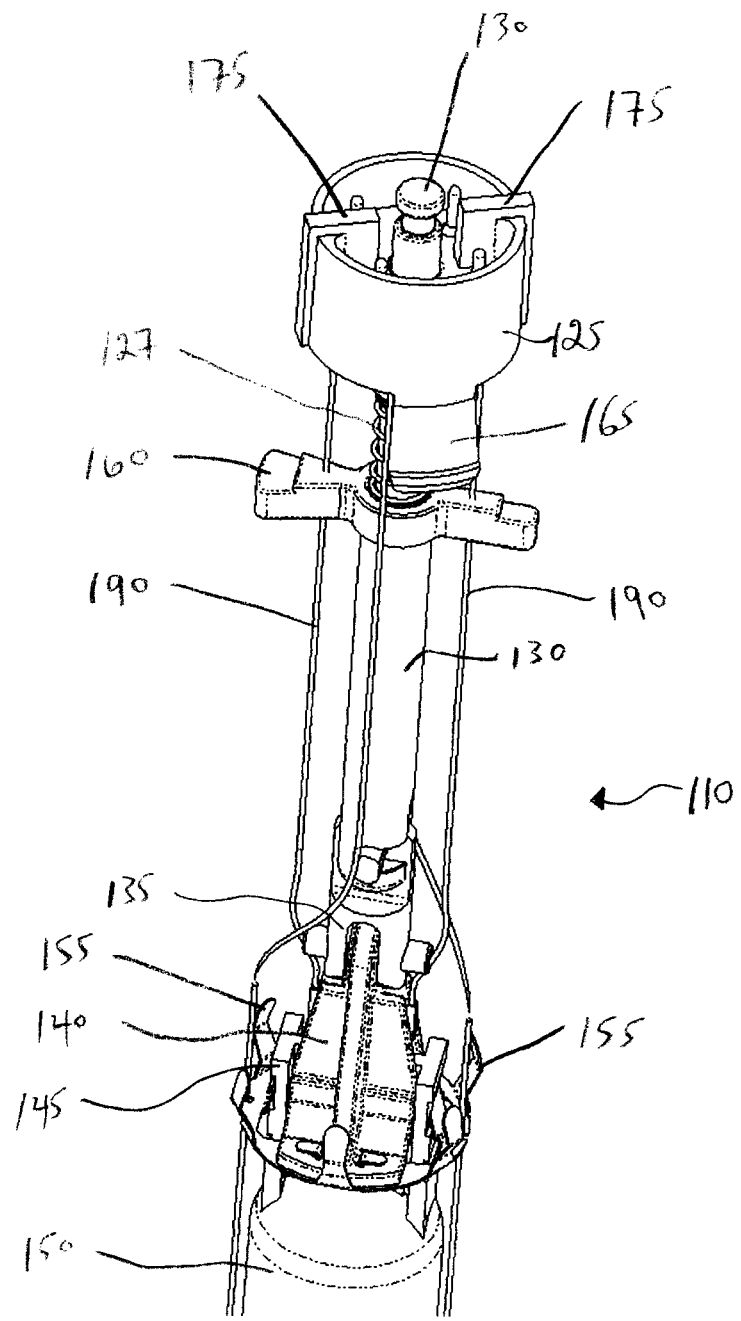
FIG. 2 illustrates an enlarged view of a distal portion of the elongate radiation source illustrated in FIG. 1.

In one of its aspects, the present invention relates to a radiation source assembly comprising an elongate radiation source; a reactor port for receiving and reversibly securing the elongate radiation source; a top plug element for reversible connection to a proximal end of the radiation source and reversible engagement with the reactor port; the top plug element configured to be disengaged from reactor port without disengagement of the elongate radiation source from the reactor port. Preferred embodiments of this radiation source assembly may include any one or a combination of any two or more of any of the following features:

- radiation source assembly comprises a first locking element for securing the elongate radiation source to the reactor port;
- the first locking element comprises a first locking portion disposed on the elongate radiation source and a second locking portion disposed on the reactor port;
- the first locking portion and the second locking portion are movable with respect to one another between: (i) a first position in which the elongate radiation source and the reactor port are engaged to one another, and (ii) a second position in which the elongate radiation source and the reactor port may be disengaged from one another;
- the first locking portion and the second locking portion are rotatably movable with respect to one another between: (i) a first position in which the elongate radiation source and the reactor port are engaged to one another, and (ii) a second position in which the elongate radiation source and the reactor port may be disengaged from one another;
- the first locking portion is rotatably movable about a longitudinal axis of the elongate radiation source between: (i) a first position in which the elongate radiation source and the reactor port are engaged to one another, and (ii) a second position in which the elongate radiation source and the reactor port may be disengaged from one another by movement of the elongate radiation source in a direction substantially parallel to the longitudinal axis;
- the first locking portion comprises a wing element and the second locking portion comprises a tab element for engagement with the wing element in the first position of the first locking portion;
- the first locking portion comprises a pair pf wing elements and the second locking portion comprises a pair of tab elements;
- the pair of wing elements are substantially diametrically opposed to one another;
- the pair of tab elements are substantially diametrically opposed to one another;
- the wing element and the tab element are configured to be engaged to one another upon movement of the elongate radiation source toward the reactor port in a direction substantially parallel to the longitudinal axis;
- the wing element and the tab element are configured to be disengaged from one another upon rotation of the elongate radiation source with respect to the reactor port about the longitudinal axis;
- the first locking portion is disposed in a lamp plug element disposed at a proximal end of the elongate radiation source;
- the lamp plug element comprises at least one electrical connection for the elongate radiation source;
- the lamp plug element comprises a plurality of electrical connections for the elongate radiation source;
- the electrical connection is an elongate pin;
- the lamp plug element comprises one half of a male-female connection unit and the top plug element comprises another half of the male-female connection unit for correct alignment of the lamp plug and the top plug element;
- the lamp plug element comprises a male portion of a male-female connection unit and the top plug element comprises a female portion the male-female connection unit for correct alignment of the lamp plug and the top plug element;
- the lamp plug element comprises a female portion of a male-female connection unit and the top plug element comprises a male portion the male-female connection unit for correct alignment of the lamp plug and the top plug element;
- the lamp plug element is configured to rotate with respect to the longitudinal axis of the elongate radiation source;
- the lamp plug element is configured to reversibly rotate with respect to the longitudinal axis of the elongate radiation source;
- the lamp plug element is coupled to a biasing element configured to urge the lamp plug element in a direction toward the top plug element;

the elongate radiation source comprises an indexing key element configured to align the elongate radiation source in a prescribed position with respect to the reactor port;

the elongate radiation source comprises an indexing key element configured to align the elongate radiation source in a single prescribed position with respect to the reactor port;

the elongate radiation source comprises a radiation-emitting cavity portion at a distal region thereof and an elongate lamp positioning portion at a proximal portion thereof;

the radiation-emitting cavity portion is configured to pivot with respect to the elongate lamp positioning portion;

the radiation source assembly further comprises a second locking element for securing the top plug element to the reactor port;

the second locking element comprises a first locking portion disposed on the reactor port and a second locking portion disposed on the top plug element;

the first locking portion and the second locking portion are movable with respect to one another between: (i) a first position in which the top plug element and the reactor port are engaged to one another, and (ii) a second position in which the top plug element and the reactor port may be disengaged from one another;

the first locking portion and the second locking portion are movable with respect to one another in a direction substantially parallel to a longitudinal axis of the elongate radiation source between: (i) a first position in which the top plug element and the reactor port are engaged to one another, and (ii) a second position in which the top plug element and the reactor port may be disengaged from one another;

the first locking portion comprises one half of a male-female connection unit and the second locking portion comprises another half of the male-female connection unit;

the first locking portion comprises a male portion of a male-female connection unit and the second locking portion comprises a female portion the male-female connection unit;

the first locking portion comprises a female portion of a male-female connection unit and the second locking portion comprises a male portion the male-female connection unit;

the first locking portion comprises a locking pin element movable between a retracted position and an extended position, and the second locking portion comprises an aperture for receiving the locking pin element;

the locking pin element is coupled to a biasing element configured to urge the locking pin element in extended position;

the locking pin element is coupled to a spring element configured to urge the locking pin element in extended position;

the locking pin element is coupled to pin release element configured to be movable between a first position in which the locking pin may not be moved and second position in which the locking pin may be moved between the retracted position and the extended position;

the top plug element comprises a positioning groove portion for receiving a positioning pin element disposed in the reactor port;

the positioning groove portion is disposed axially on a surface of the top plug element;

the positioning groove portion comprises a receptacle portion disposed in an intermediate section of the position groove portion, the receptacle portion configured to received at least a portion of the positioning element;

the radiation source assembly further comprises a sealing element disposed between the top plug element and the reactor port, the sealing element configured to create a substantially fluid tight seal when the top plug element is configured to the reactor port;

the sealing element is disposed in the reactor port;

the sealing element is disposed in the top plug element;

a first sealing element disposed in the reactor port and a second sealing element disposed in the top plug element;

the reactor port is coupled to a radiation transparent protective sleeve configured to receive the elongate radiation source;

the radiation transparent protective sleeve comprises a proximal open end and a distal closed end;

a proximal end of the radiation transparent protective sleeve comprises a sealing element to substantially prevent ingress of fluid to the interior of the protective sleeve;

the protective sleeve is constructed of quartz;

the elongate radiation source comprises at least one centering ring to maintain the elongate radiation source and the radiation transparent protective sleeve in a spaced (e.g., substantially coaxial) relationship with one another;

the elongate radiation source comprises a plurality of centering rings to maintain the elongate radiation source and the radiation transparent protective sleeve in a spaced (e.g., substantially coaxial) relationship with one another;

the elongate radiation source is an ultraviolet radiation source;

the elongate radiation source is a low pressure ultraviolet radiation source;

the elongate radiation source is a low pressure, high output ultraviolet radiation source; and the elongate radiation source is medium pressure ultraviolet radiation source.

Another aspect of the present invention relates to a radiation source module comprising a support element for securing the module in a fluid treatment system and at least one radiation source assembly (preferably a plurality) as defined above.

Another aspect of the present invention relates to a fluid treatment system comprising a fluid treatment zone for receiving a flow of fluid and at least one radiation source module defined in the previous paragraph, wherein the at least one radiation source module is configured such that the radiation source assembly is disposed in the fluid treatment zone. Another aspect of the present invention relates to a fluid treatment system comprising a fluid treatment zone for receiving a flow of fluid and at least one radiation source assembly defined in above disposed in the fluid treatment zone. Preferred embodiments of either of these fluid treatment systems may include any one or a combination of any two or more of any of the following features:

the fluid treatment zone may be comprised in an open channel for receiving the flow of fluid;

the fluid treatment zone may be comprised in a closed channel for receiving the flow of fluid;

the at least one radiation source assembly may have a longitudinal axis disposed transverse to the direction of fluid flow through the fluid treatment zone;

the at least one radiation source assembly may have a longitudinal axis disposed orthogonal to the direction of fluid flow through the fluid treatment zone;

the at least one radiation source assembly may be disposed substantially vertically in the fluid treatment zone.

With reference to FIGS. 1-14, there is illustrated a radiation source assembly 100. Radiation source assembly 100 comprises an elongate radiation source 110, a reactor port 115, and a top plug element 120.

Elongate radiation source 110 comprises a lamp plug 125 which is coupled to a lamp positioning rod 130. Lamp positioning rod 130 is coupled to one end of a universal joint 135. The other end of universal joint 135 is coupled to a ceramic element 140 that is coupled to a pinch 145 disposed at the end of a radiation lamp 150. A series of tab elements 155 are connected to ceramic element 140 and serve to position radiation source 110 in a protective sleeve 117 attached (preferably in a substantially fluid tight manner) to reactor port 115 (discussed in more detail below).

Attached to lamp position rod 130 is an indexing key 160, the purpose of which will be described in more detail below. Disposed between indexing key 160 and lamp plug 125 is a spring 127. Spring 127 serves the purposes of biasing lamp plug 125 toward top plug 120 to facilitate maintain an electrical connect therebetween.

Figure 13:
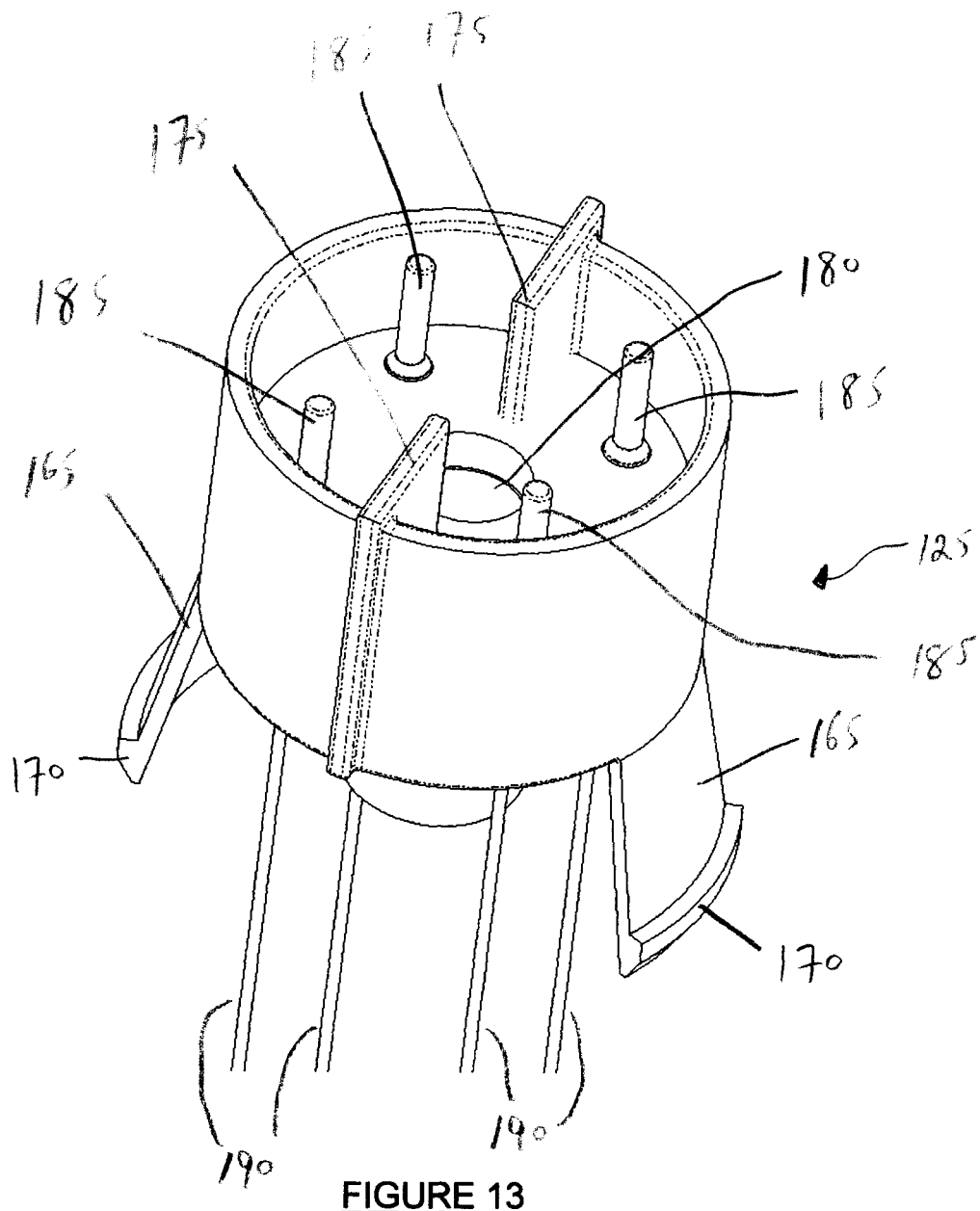
FIG. 13 illustrates an enlarged perspective view of the portion of the elongate radiation source illustrated in FIG. 1.

With particular reference to FIG. 13, it can be seen that lamp plug 125 comprises a pair of locking wings 165. Each locking wing 165 has a locking edge 170. Lamp plug 125 also includes a pair of alignment tabs 175 which are configured to provide a complementary fit with alignment slots disposed in top plug 120 (discussed in more detail below). Lamp plug 125 further comprises an aperture 180 for receiving a proximal end portion of lamp positioning rod 130 (see FIG. 2). Lamp plug 125 further comprises four electrical pins 185 each of which is connected to one end of an electrical lead 190. The other end of each electrical lead 190 is connected to lamp 150.

Figure 11:
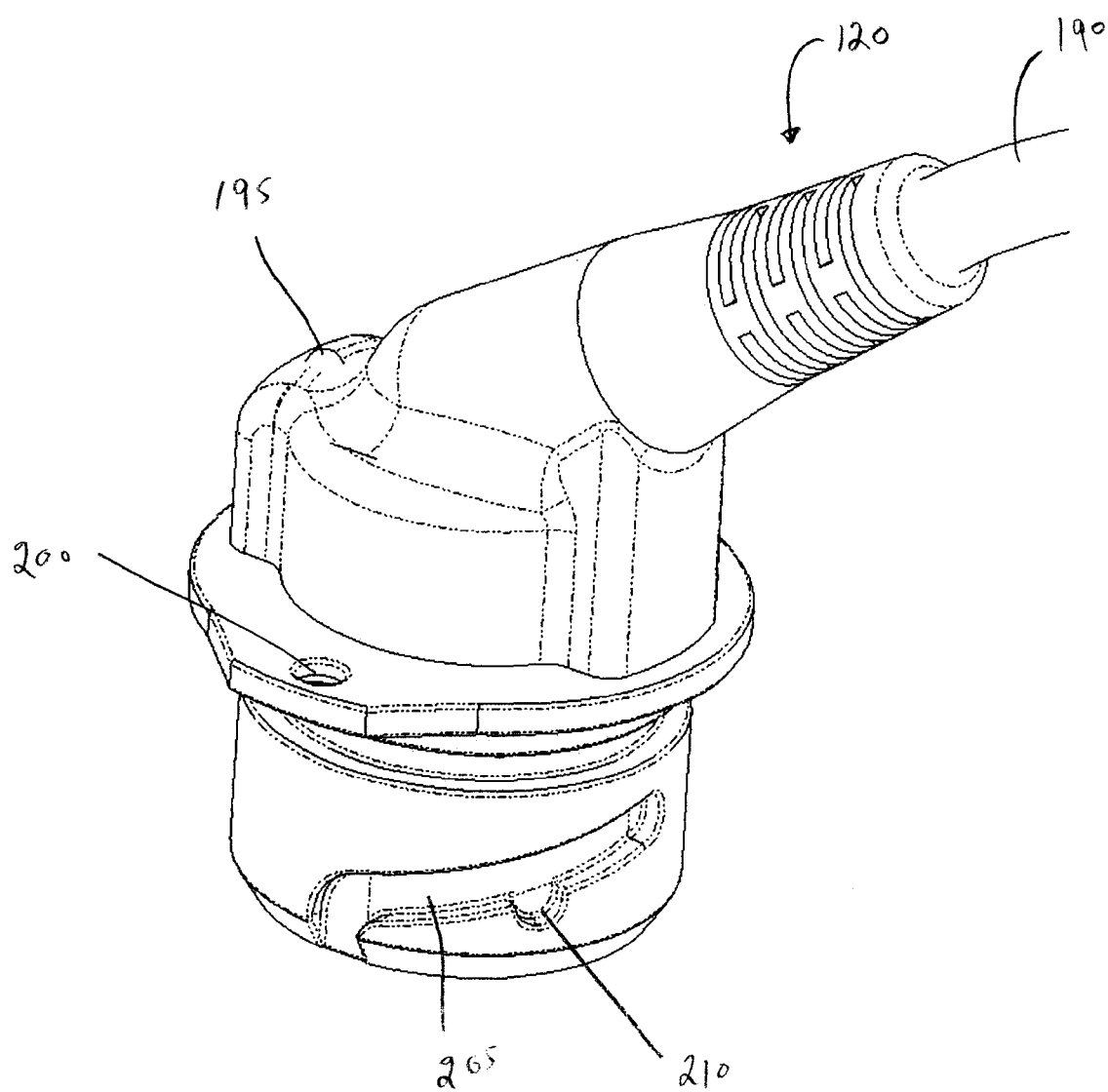
FIGS. 11 and 12 illustrate perspective views of the top plug element in the radiation source assembly illustrated in FIG. 1.
Figure 12:
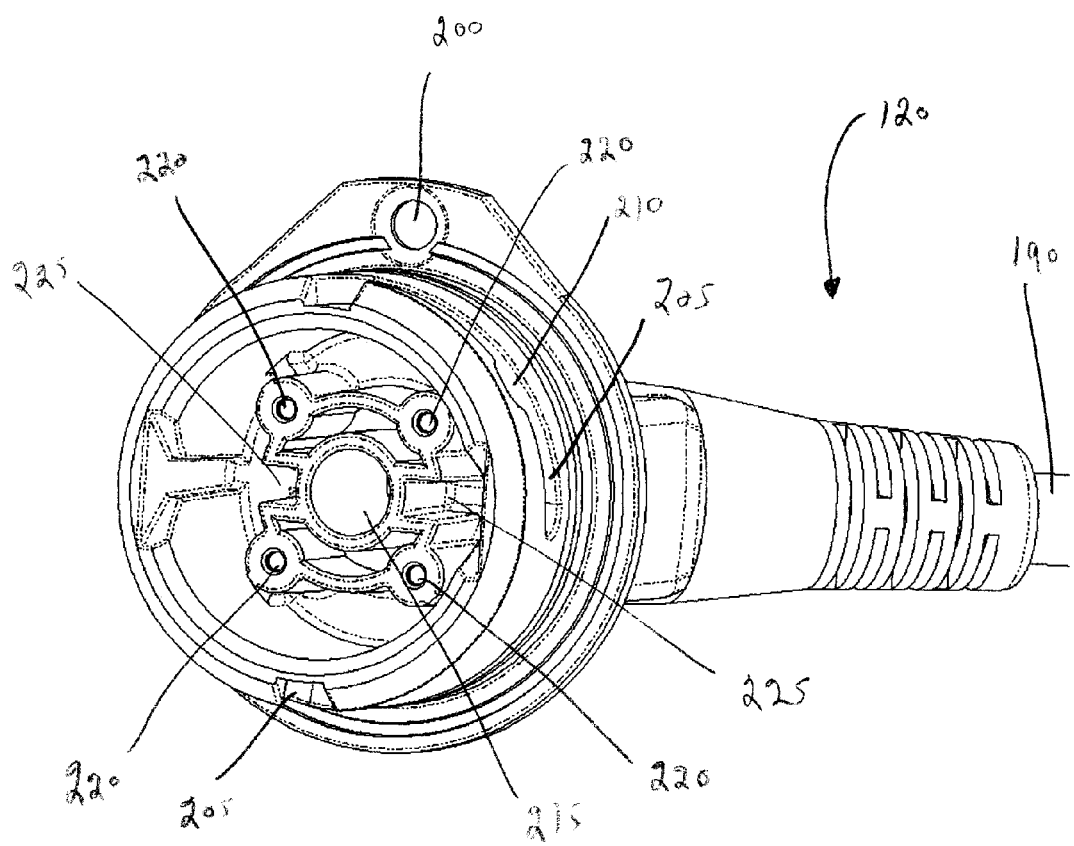

With particular reference to FIGS. 11 and 12, it can be seen that top plug 120 comprises a conduit 190 in which is disposed an electrical supply line (not shown for clarity). Top plug 120 further comprises an LED indicator 195 which provides a visual indicator to an operator that power is being supplied to elongate radiation source 110.

Top plug 120 further comprises an aperture 200 for receiving a locking pin disposed on reactor port 115 (described in more detail below).

Top plug 120 further comprises a positioning groove 205 for receiving a positioning pin disposed in reactor port 115 (described in more detail below). Positioning groove 205 includes a receptacle portion 210, the purpose and function of which will be described in more detail below. It should be understood that a second positioning groove 205 is provided on the opposite side of top plug 120 but is not shown in FIG. 11 for clarity.

Top plug 120 comprises an aperture 215 for receiving a proximal end of positioning rod 130 of elongate radiation source 110. Further, top plug 120 comprises four electrical receptacles 220 for receiving electrical pins 185 disposed in lamp plug 125. A pair of alignment slots 225 are also provided in top plug 120 and are configured to provide a complementary fit with alignment tabs 175 disposed in lamp plug 125.

Figure 14:
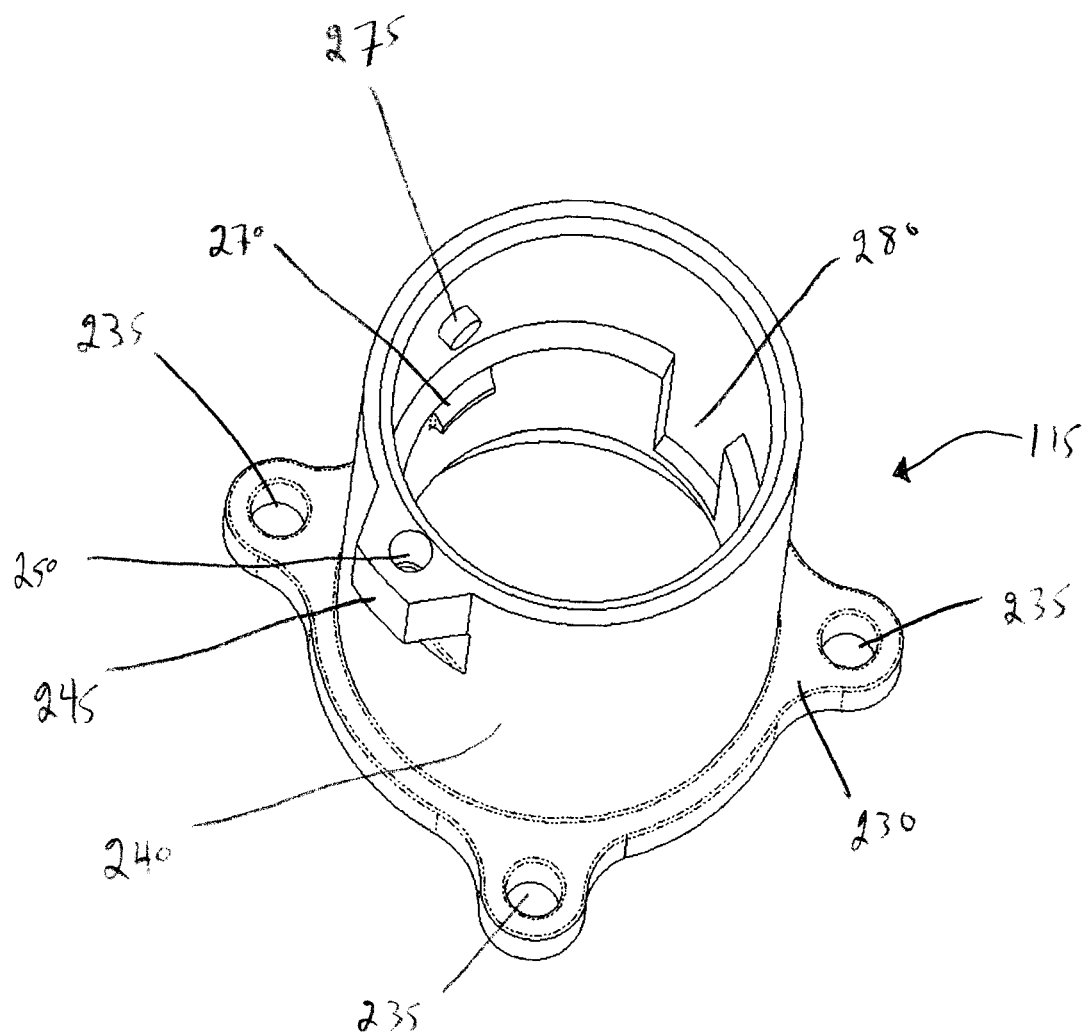
FIG. 14 illustrates an enlarged perspective view of the reactor port of the radiation source assembly illustrated in FIG. 1.

With particular reference to FIG. 14, it can be seen that reactor port 115 comprises a base portion 230 having a series of mounting apertures 235. Base portion 230 is mounted in a fluid treatment system (not shown for clarity) via mounting apertures 235.

Reactor port 115 comprises a housing 240. Attached to the outside of housing 240 is a platform 245 having an aperture 250 configured to receive a locking pin 260 (see FIGS. 1-10). Locking pin 260 is preferably spring loaded and is coupled to a slide switch 265 which is operable between a first position in which locking pin 260 is locked in an extended position and a second position in which locking pin 260 may be at least partially retracted into aperture 250.

Housing 240 further comprises a pair of locking tabs 270 (only one is shown for clarity in FIG. 14) which are configured to engage and lock with respect to locking edge 170 of locking wings 165 of lamp plug 125.

Housing 240 further comprises a pair of positioning pins 275 which are configured to engage with positioning groove 205 of top plug 120. Housing 240 further comprises a pair of slot portions 280 (only one is shown for clarity in FIG. 14) which are configured to receive indexing key 160 of elongate radiation source 110.

Radiation source assembly 100 is assembled by initially installing elongate radiation 110 in reactor port 115 and thereafter connecting top plug 120 to reactor port 115 thereby establishing an electrical connection between top plug 120 and elongate radiation source 110. This sequential approach in assembling radiation source assembly 110 is reversed when it is desired to replace or otherwise service elongate radiation source assembly 110. In other words, it will be clear from the description below that, in normal operation, electrical power can not be supplied to elongate radiation source 110 unless it is installed in reactor port 115 prior to engagement of top plug 120 and reactor port 115. This is a significant advantage of the present invention.

Figure 3:
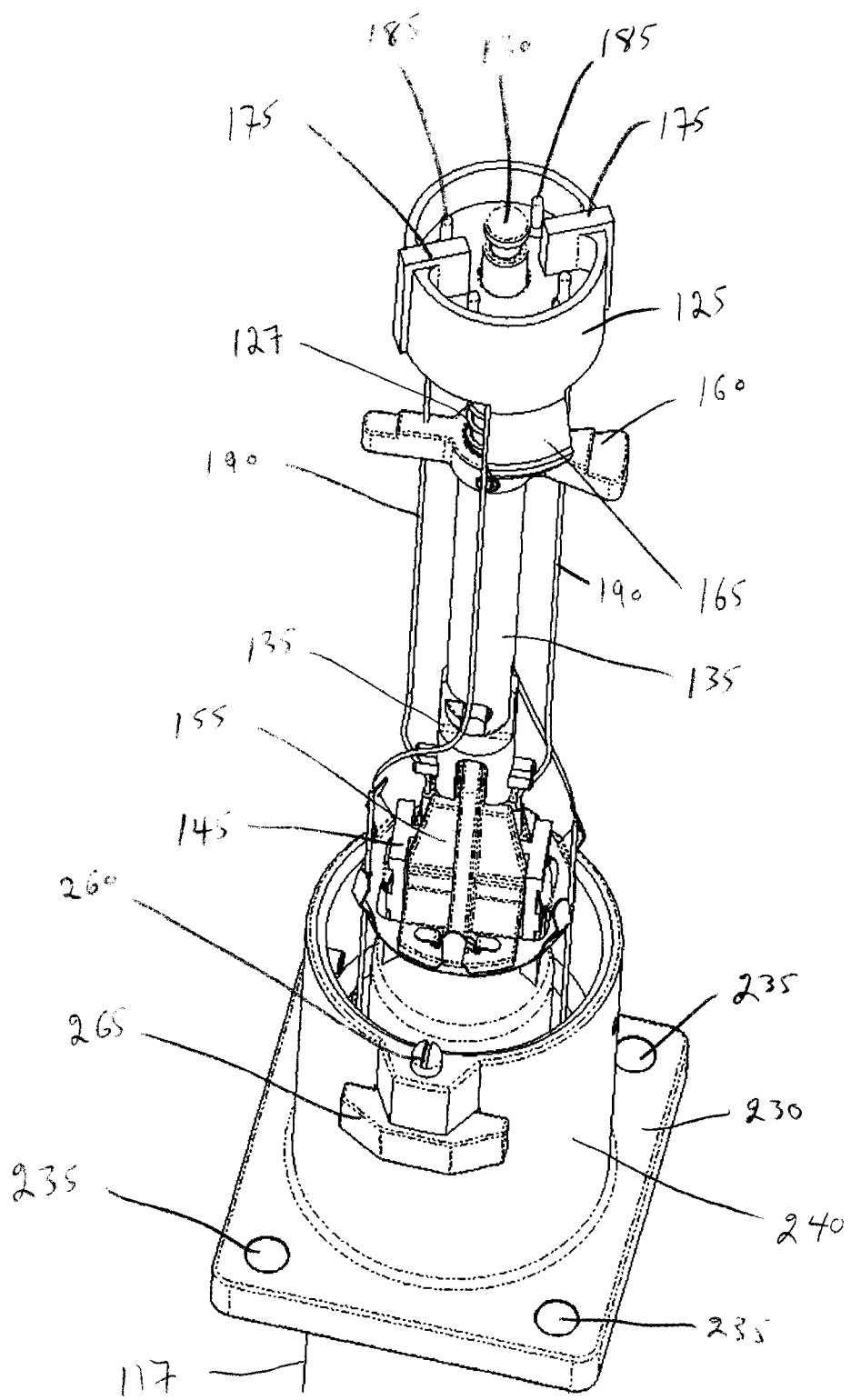
FIGS. 3 and 4 illustrate sequential insertion of the elongate radiation source illustrated in FIG. 2 into the reactor port illustrated in FIG. 1.
Figure 4:
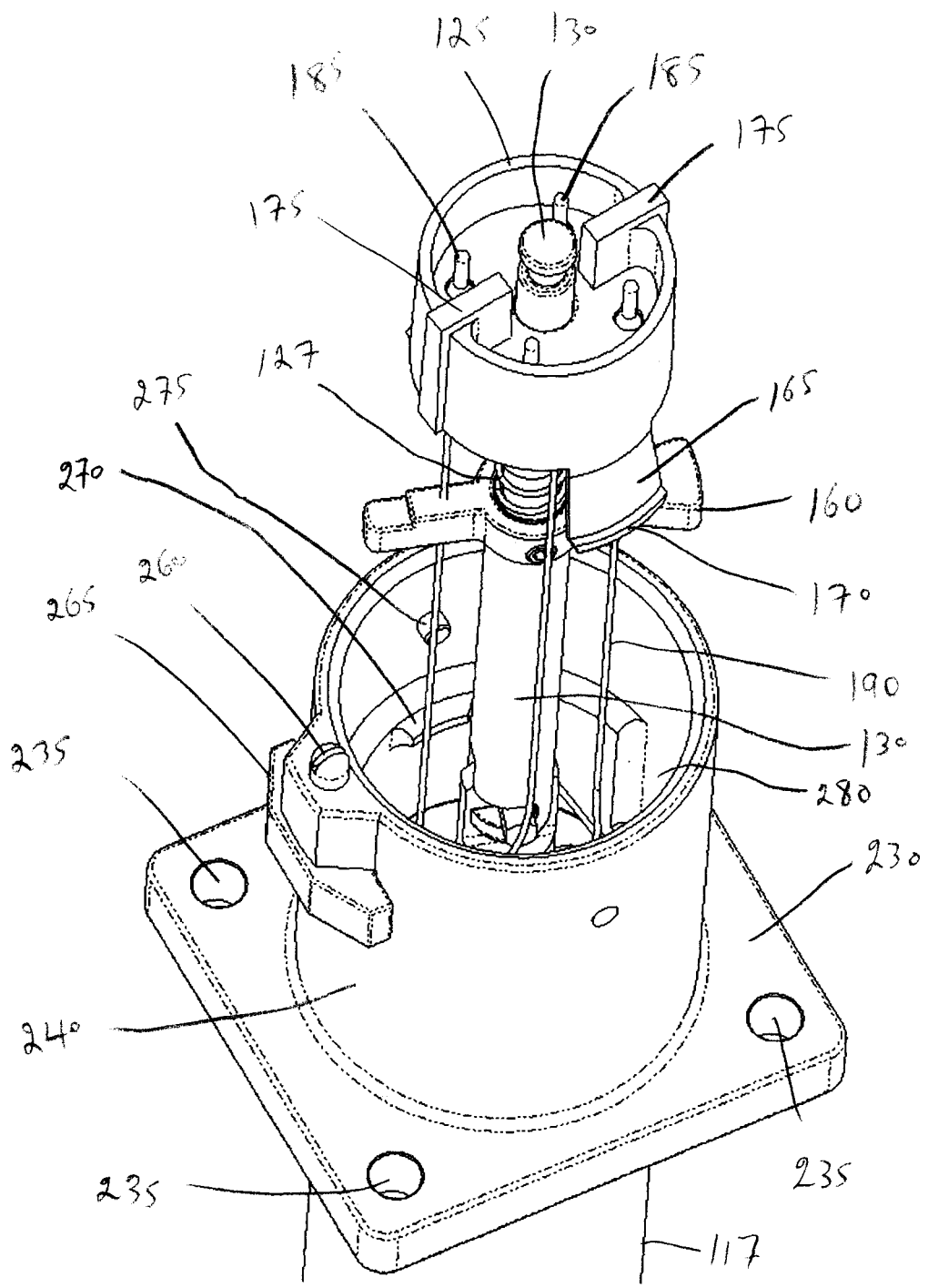
Figure 5:
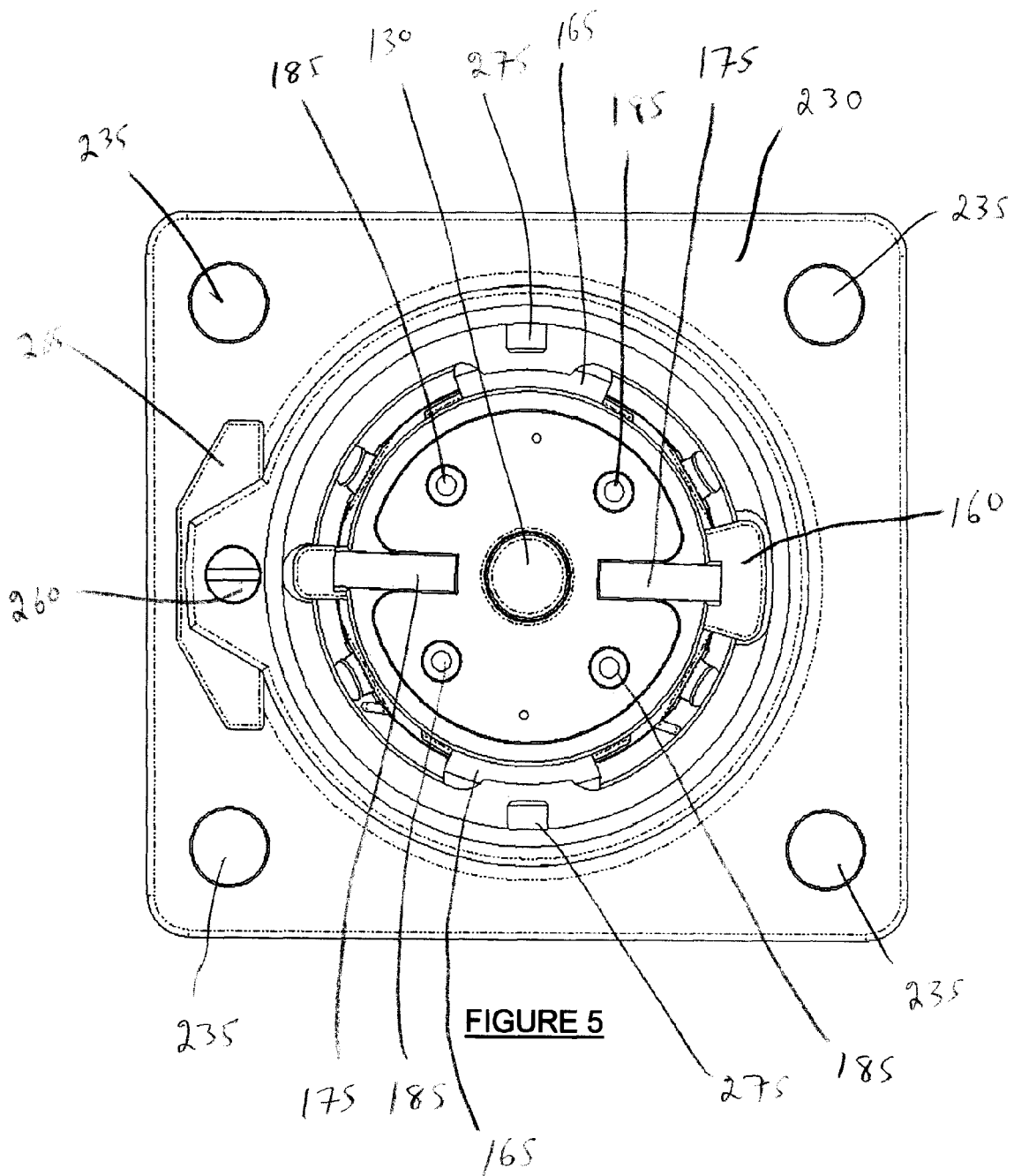
FIG. 5 illustrates a top view of the present radiation source assembly after installation of the elongate radiation lamp into the reactor port.
Figure 6:
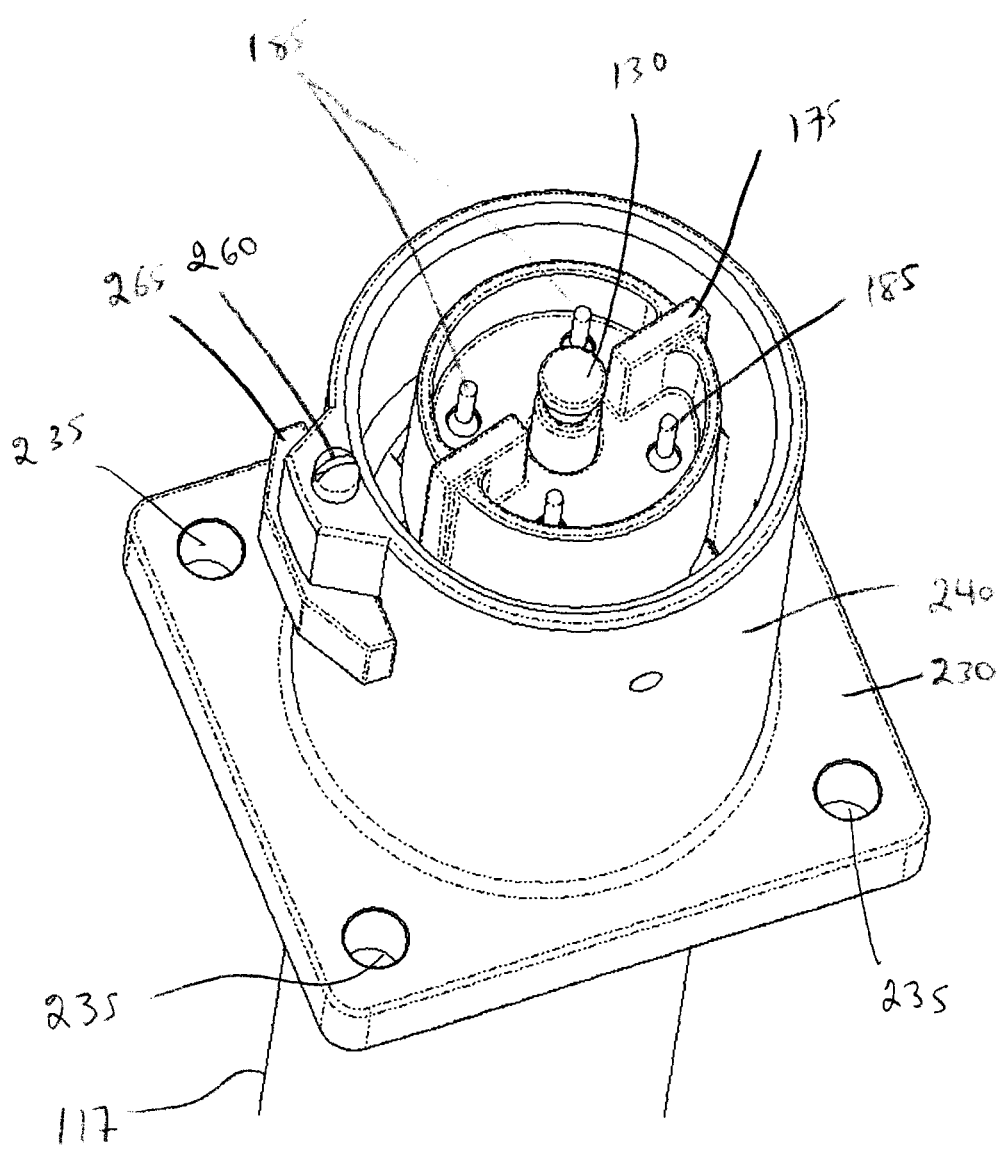
FIGS. 6-8 illustrate various perspective views of the radiation source assembly after installation of the elongate radiation source into the reactor port.
Figure 7:
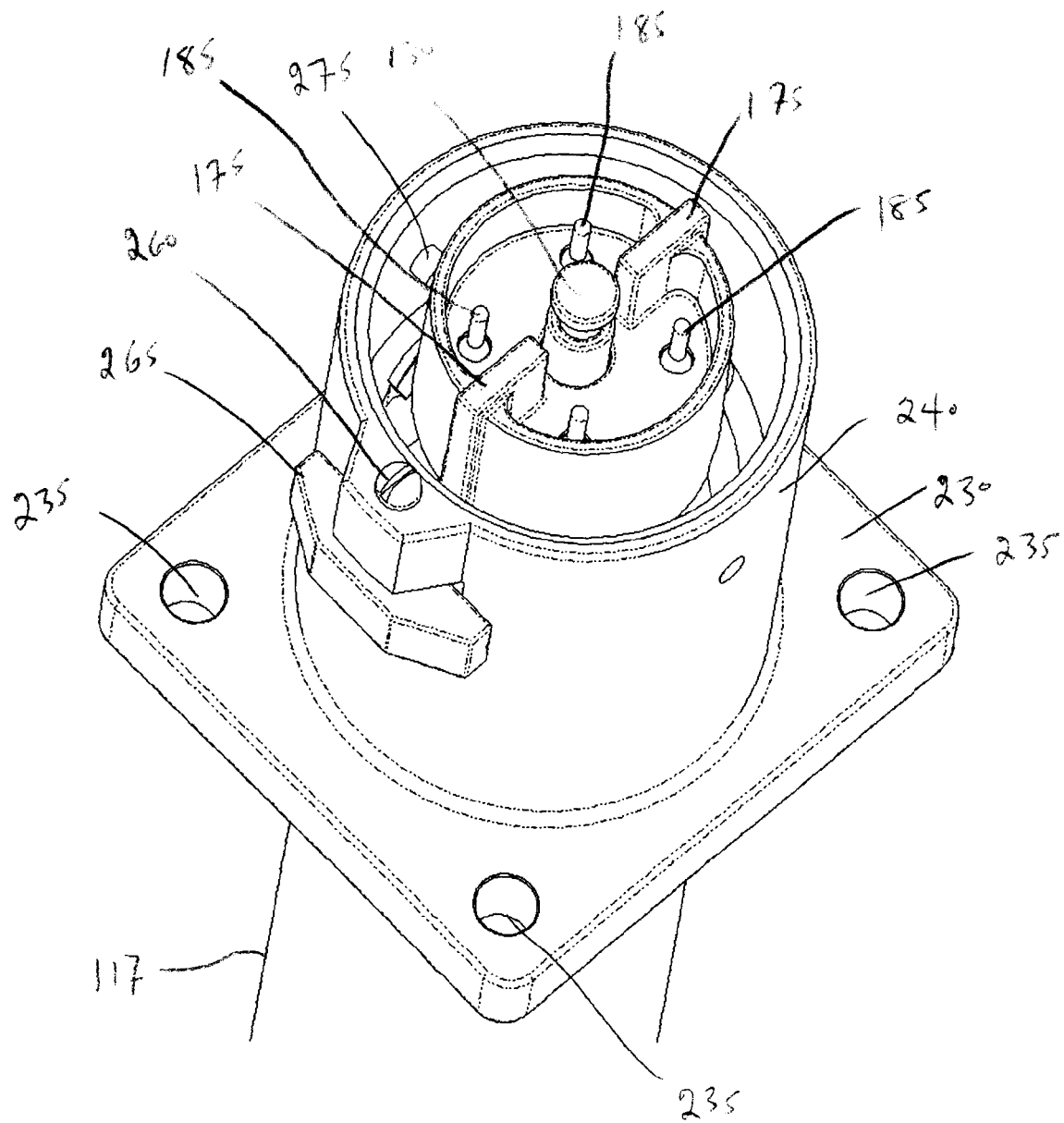
Figure 8:
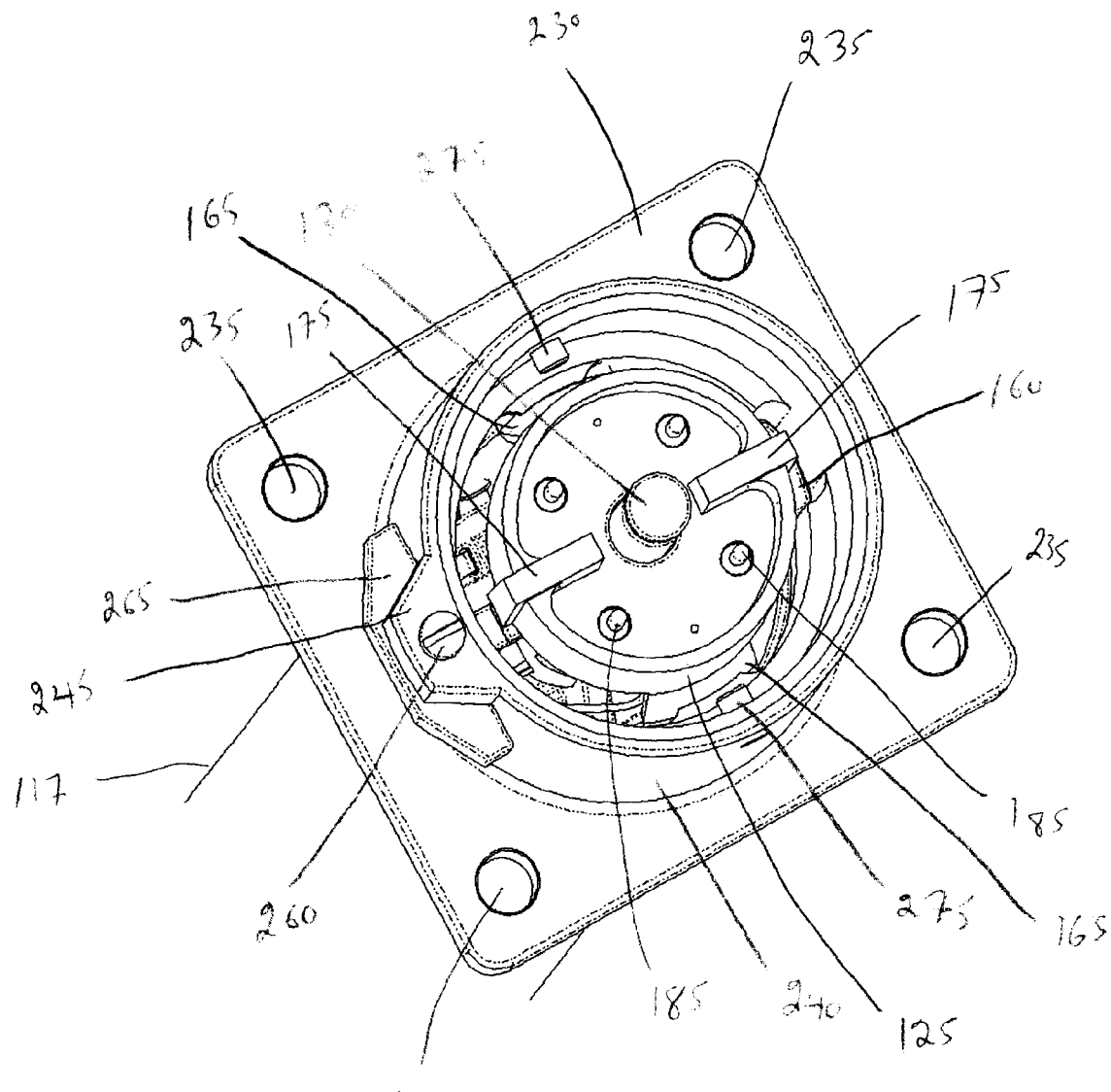

Thus, elongate radiation source 110 is disposed in reactor port 115 as shown in FIG. 1 and is continued to be moved downwardly into reactor port 115—see FIGS. 3 and 4.

As lamp plug 125 of elongate radiation source 110 approaches housing 240 of reactor port 115, indexing key 160 is aligned with slots 280 on the inside of housing 240. As will be appreciated, the shape of indexing key 160 and slots 280 necessitates only a single correct position of elongate radiation source 110 with respect to reactor port 115. As lamp plug 125 enters housing 240 of reactor port 115, locking wings 165 of lamp plug 125 are biased inwardly until locking edges 170 of locking wings 165 clear locking tabs 270 disposed on the interior of housing 240.

Figure 9:
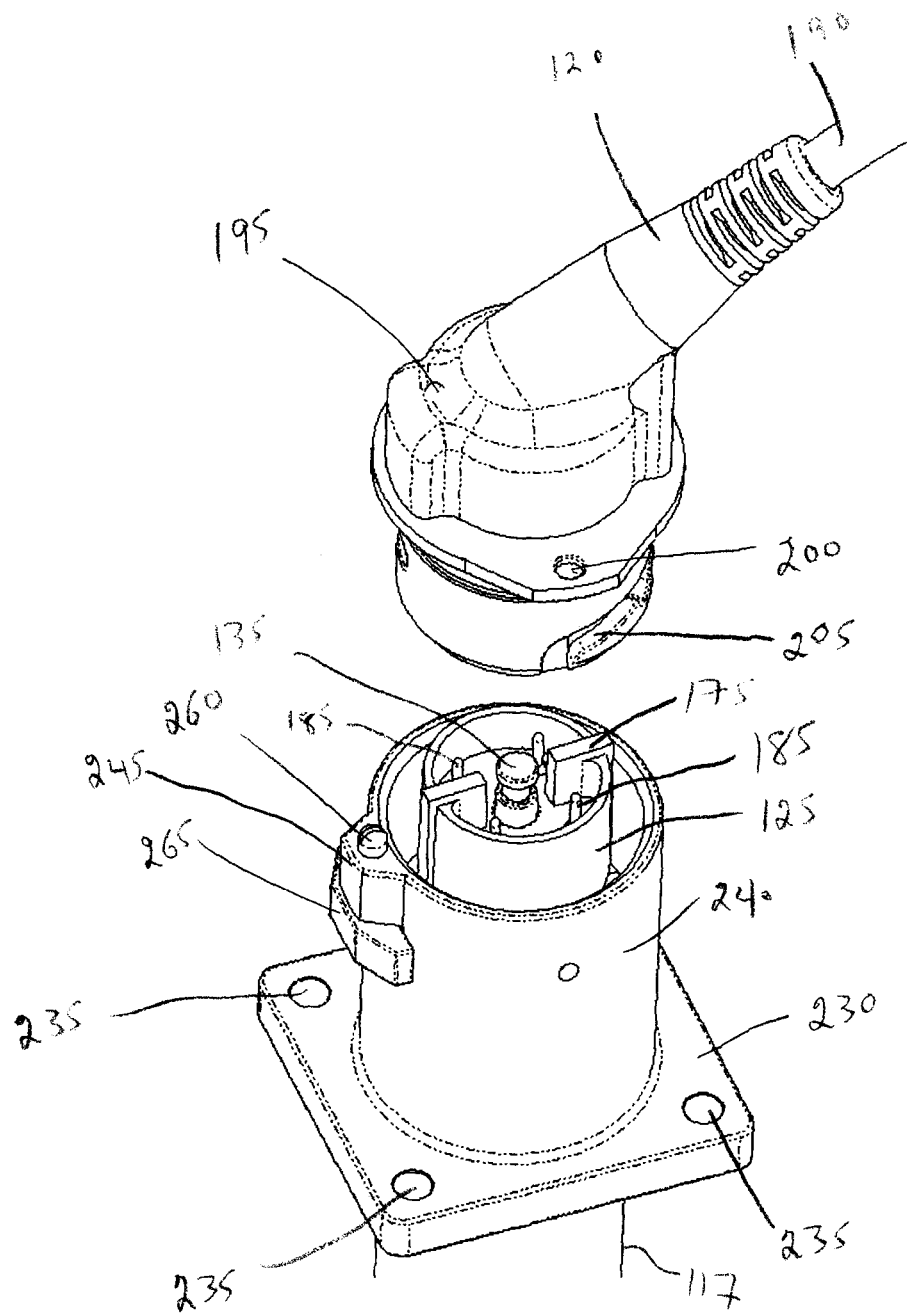
FIG. 9 illustrates the top plug element being disposed above the reactor port after installation of the elongate radiation source.
Figure 10:
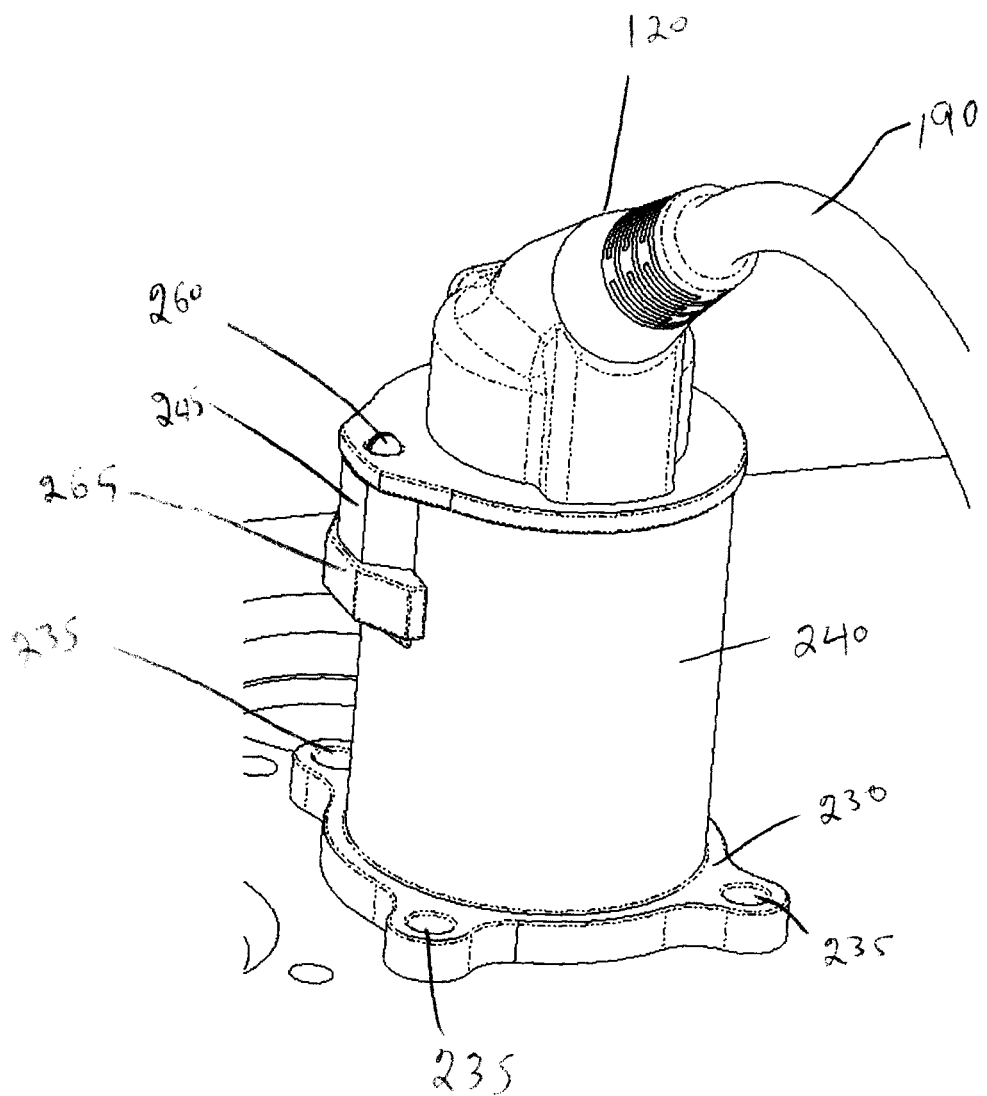
FIG. 10 illustrates the radiation source assembly illustrated in FIG. 1 after installation of the elongate radiation source and coupling of the top plug element to the reactor port.

Next, top plug 120 is placed over the combination of installed elongate radiation source 110 and reactor port 115—see FIG. 9. Top plug 120 is lowered toward housing 120 of reactor port 115 in a manner such that positioning pins 275 on the inside of housing 240 are aligned with the entry of positioning groove 205 of top plug 120. Top plug 120 is pushed down such that locking edges 170 of locking wings 265 clear locking tabs 270 of housing 240, locking wings 265 snap back into the original position thereby locking lamp plug 125 into reactor port 115. At this point, it is not possible to withdraw elongate radiation source 110 simply by lifting its straight out of reactor port 115. FIGS. 5-8 illustrate this configuration of the assembly. Once this is achieved, top plug 120 is rotated such that locating pin 275 follows locating groove 205 resulting in aperture 200 of top plug 120 moving toward aperture 250 of reactor port 115. Next, slide switch 265 is depressed by the action of rotating top plug 120 which allows locking pin 260 to be at least partially retracted into aperture 250. Once aperture 200 and top plug 120 is aligned with aperture 250 in reactor port 115, locking pin 260, being spring loaded, extends into aperture 200 of top plug 120 thereby securely engaging top plug 120 to reactor port 115.

When it is desired to replace or otherwise service elongate radiation source 110, the above steps are reversed. Importantly, if electrical power is mistakenly not turned off at the source prior to replacement or servicing of elongate radiation source 110, the service operator is not subject to exposure to harmful radiation since top plug 120 must be removed prior to removal of elongate radiation source 110. This prevents the service operator from removing elongate radiation source 110 with power still connected and exposing the operator to the deleterious effects of ultraviolet radiation.

Once the service operator wishes to remove top plug 120 from reactor port 115, slide switch 265 is actuated allowing the operator to depress locking pin 260 and twist top plug 120 with respect to reactor port 115 thereby moving locator pin 275 of housing 240 with respect to locating groove 205 of top plug 120. If protective sleeve 117 in which elongate radiation source 100 has been disposed is cracked, broken or otherwise comprised resulting in flooding of the radiation source assembly with pressurized fluid, the pressurized fluid will force locking pin 275 of housing 240 to reside in receptacle 210 of locating groove 205. This will warn the service operator that there is a problem with pressurized fluid in the radiation source assembly and the service operator may then turn off the flow of fluid in the fluid treatment system thereby to reduce the fluid pressure prior to removal of top plug 120 from reactor port 115. This is another advantage of the present radiation source assembly and provide additional safety for the service operator in avoiding having a build up of pressurized fluid blast top plug 120 away from reactor port 115 thereby potentially injuring the service operator and/or those around him/her.

Once top plug 120 has been removed from reactor port 115, elongate radiation source 110 may be removed from reactor port 115 by rotating lamp plug 125 until locking wings 265 of lamp plug 125 clear locking tabs 270 of housing 240 of reactor port 115. At this point, elongate radiation source 110 may be fully retracted from reactor port 115.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A radiation source assembly comprising:
an elongate radiation source;
a reactor port for receiving and reversibly securing the elongate radiation source; and
a top plug element for reversible connection to a proximal end of the radiation source and reversible engagement with the reactor port;
the top plug element being configured to be disengaged from the reactor port without disengagement of the elongate radiation source from the reactor port;
the top plug element having a positioning groove disposed circumferentially on an outer surface of the top plug element and configured to receive a positioning pin element disposed on the reactor port;
the top plug element having a receptacle portion disposed in said groove and configured to receive and detain at least a portion of the positioning pin element.

2. The radiation source assembly defined in claim 1, further comprising a first locking element for securing the elongate radiation source to the reactor port.

3. The radiation source assembly defined in claim 2, wherein the first locking element comprises a first locking portion disposed on the elongate radiation source and a second locking portion disposed on the reactor port.

4. The radiation source assembly defined in claim 3, wherein the first locking portion and the second locking portion are movable with respect to one another between: (i) a first position in which the elongate radiation source and the reactor port are engaged to one another, and (ii) a second position in which the elongate radiation source and the reactor port may be disengaged from one another.

5. The radiation source assembly defined claim 3, wherein the first locking portion comprises a wing element and the second locking portion comprises a tab element for engagement with the wing element in the first position of the first locking portion.

6. The radiation source assembly defined in claim 5, wherein the wing element and the tab element are configured to be engaged to one another upon movement of the elongate radiation source toward the reactor port in a direction substantially parallel to the longitudinal axis.

7. The radiation source assembly defined in claim 5, wherein the wing element and the tab element are configured to be disengaged from one another upon rotation of the elongate radiation source with respect to the reactor port about the longitudinal axis.

8. The radiation source assembly defined in claim 3, wherein the first locking portion is disposed in a lamp plug element disposed at a proximal end of the elongate radiation source.

9. The radiation source assembly defined in claim 8, wherein the lamp plug element is configured to rotate with respect to the longitudinal axis of the elongate radiation source.

10. The radiation source assembly defined in claim 2, further comprising a second locking element for securing the top plug element to the reactor port.

11. The radiation source assembly defined in claim 10, wherein the first locking portion and the second locking portion are movable with respect to one another between: (i) a first position in which the top plug element and the reactor port are engaged to one another, and (ii) a second position in which the top plug element and the reactor port may be disengaged from one another.

12. The radiation source assembly defined in claim 1, wherein the top plug element comprises a positioning groove portion for receiving a positioning pin element disposed in the reactor port.

13. The radiation source assembly defined in claim 1, further comprising a sealing element disposed between the top plug element and the reactor port, the sealing element configured to create a substantially fluid tight seal when the top plug element is configured to the reactor port.

14. The radiation source assembly defined in claim 1, wherein the reactor port is coupled to a radiation transparent protective sleeve configured to receive the elongate radiation source.

15. The radiation source assembly defined in claim 14, wherein the elongate radiation source comprises at least one centering ring to maintain the elongate radiation source and the radiation transparent protective sleeve in a spaced (e.g., substantially coaxial) relationship with one another.

16. A radiation source module comprising a support element for securing the radiation source module in a fluid treatment system, and at least one radiation source assembly defined in claim 1 secured to the support element.

17. A fluid treatment system comprising a fluid treatment zone for receiving a flow of fluid and at least one radiation source module defined claim 16, wherein the at least one radiation source module is configured such that the radiation source assembly is disposed in the fluid treatment zone.

18. A fluid treatment system comprising a fluid treatment zone for receiving a flow of fluid and at least one radiation source assembly defined in claim 1 disposed in the fluid treatment zone.

19. The fluid treatment system defined in claim 18, wherein the at least one radiation source assembly has a longitudinal axis disposed transverse to the direction of fluid flow through the fluid treatment zone.

* * * * *